US009645092B2

(12) United States Patent
Lowe et al.

(10) Patent No.: US 9,645,092 B2
(45) Date of Patent: May 9, 2017

(54) DEVICE AND METHOD FOR VERIFYING THE CONSTRUCTION OF ADHESIVELY-ATTACHED SUBSTRATES

(71) Applicant: Valco Cincinnati, Inc., Cincinnati, OH (US)

(72) Inventors: Kevin James Lowe, Coquitlam (CA); Graham Terence Manders, Vancouver (CA); Stelian Nicolaie Vasiu, Burnaby (CA); James Brashear, Mason, OH (US); Aiqiu Zuo, Burnaby (CA); Denis Tran, Burnaby (CA); Mehdi Bahrami, Vancouver (CA)

(73) Assignee: Valco Cincinnati, Inc., Cincinnati, OH (US)

( * ) Notice: Subject to any disclaimer, the term of this patent is extended or adjusted under 35 U.S.C. 154(b) by 283 days.

(21) Appl. No.: 14/052,978

(22) Filed: Oct. 14, 2013

(65) Prior Publication Data
US 2015/0104563 A1    Apr. 16, 2015

(51) Int. Cl.
*B32B 41/00* (2006.01)
*G01N 21/88* (2006.01)
(Continued)

(52) U.S. Cl.
CPC ......... *G01N 21/8806* (2013.01); *B32B 41/00* (2013.01); *B65B 51/02* (2013.01);
(Continued)

(58) Field of Classification Search
CPC ..... B32B 2041/04; B32B 41/00; G01B 11/22; G01N 25/72
See application file for complete search history.

(56) References Cited

U.S. PATENT DOCUMENTS 5,582,663 A    12/1996    Matsunaga
5,827,162 A    10/1998    Rubin et al.
(Continued)

FOREIGN PATENT DOCUMENTS

EP    2453225 A2    5/2012
GB    2289941 A    12/1995
GB    2331150 A    5/1999

OTHER PUBLICATIONS

EP Search Report pertaining to EP14188905.5, 7 pages.
European Examination Report dated Mar. 18, 2016 pertaining to European Patent Application No. 14 188 905.5.

*Primary Examiner* — Xiao Zhao
(74) *Attorney, Agent, or Firm* — Dinsmore & Shohl LLP (57) ABSTRACT

A device and method for inspecting the deposition of hot melt onto an object to be assembled. A comparison is made between sensed images of the object after application of the hot melt and a predetermined standard to determine if the construction integrity of the object made with the hot melt is within the range established by the standard. Composite images from a sensor operating in the infrared band and another sensor reveal physical features of the object, as well as provide registration information about the placement of the hot melt on the assembled object. Composite images also present a way to visually ascertain ongoing or past production operations in order to trace problems with the raw material used for the object, as well as for the construction process of the object with the hot melt.

15 Claims, 6 Drawing Sheets

(51) Int. Cl.
*G01N 25/72* (2006.01)
*B65B 51/02* (2006.01)
*C09J 5/06* (2006.01)
*G01B 11/22* (2006.01)

(52) U.S. Cl.
CPC ............... *C09J 5/06* (2013.01); *G01B 11/22* (2013.01); *G01N 25/72* (2013.01); *B32B 2041/04* (2013.01)

(56) References Cited

U.S. PATENT DOCUMENTS

| | | | |
|---|---|---|---|
| 6,129,503 A | 10/2000 | Schenone | |
| 6,567,167 B1* | 5/2003 | Chou | G02B 6/272 356/365 |
| 8,073,239 B1 | 12/2011 | Bahrami et al. | |
| 8,520,929 B1 | 8/2013 | Murray et al. | |
| 2005/0041723 A1 | 2/2005 | Heerdt et al. | |
| 2007/0237385 A1* | 10/2007 | Kato | G01N 21/9501 382/149 |
| 2009/0196489 A1* | 8/2009 | Le | G01N 21/9503 382/148 |
| 2010/0100275 A1 | 4/2010 | Mian et al. | |
| 2010/0320386 A1 | 12/2010 | Gaon | |

\* cited by examiner

DEVICE AND METHOD FOR VERIFYING THE CONSTRUCTION OF ADHESIVELY-ATTACHED SUBSTRATES

BACKGROUND OF THE INVENTION

This invention relates generally to a system to verify the construction of products requiring heated adhesive for assembly, and more particularly to a system for comparing the quality of adhesive-deposition operations on assembled products as well as provisions for taking corrective measures in circumstances when an adhesive deposition is such that it causes an assembled product to fall outside of an acceptable quality range.

Modern fabrication methods have increasingly taken advantage of adhesive joining to contribute to lighter-weight, more efficient assembled structures than conventional fastening approaches. Such methods have been useful in discrete manufacturing as well as continuous flow manufacturing on a conveyor line, including those used in conjunction with hot melt potting of electronic parts, product assembly with hand-guns configured to dispense hot melt adhesive, or other assembly techniques. Moreover, such approaches may be used with numerous substrates, including metals, woods, plastics, composites, paper-based materials or the like. In one example, containers for product packaging are frequently constructed from boxes that are folded from generally planar corrugated paper-based blanks or related substrates. Typical fabrication involves a series of forming operations such as those that may be performed by a packaging machine such as a case sealer or cartoner. In the present context, the terms "hot melt", "adhesive", hot melt adhesive" or the like are used interchangeably herein to cover various scenarios where hot melt is used; whether a more particular application (such as an adhesive) is intended will be apparent from the context.

As mentioned above, the glue application step typically involves depositing adhesive in either continuous or discrete fashion. Such adhesive deposition is subject to errors that can render the assembled product unacceptable for its intended purpose. To that end, sensors have been used to detect the presence of a deposited glue or related adhesive. While such sensors may be satisfactory for verification of the presence of glue—usually on a per-bead basis—present on a blank in a well-controlled environment, they are inadequate to check as to whether the overall pattern of glue laid down is correctly, especially in high-speed operational environments where automated assembly takes place. In addition, such sensing technology is usually not capable of accurately measuring glue quantity or placement since either many sensors must be used—one for each bead—or the sensors are subject to interference from the environment such as with thermal sensors. Thus, in situations where it is desirable to perform a more comprehensive assessment of the adhesive being deposited, single point sensors are often not adequate. Arrays of such devices arranged as imaging sensors may enhance the ability to adequately represent the deposition of adhesive onto a substrate or blank; however, such additional sensor arrays may significantly contribute to overall system cost and complexity. Moreover, to the extent that they may help assess the presence or absence of adhesive deposition in a particular location on the blank surface, they do not provide such information once direct access to the adhesive is obscured, such as by being covered by overlaid or other adjacent surfaces of the assembled item. In addition, they provide only numerical feedback regarding the glue position or length of the glue beads, for example, which can be difficult for processing equipment to filter and interpret for the user.

Furthermore, neither form of sensor is capable of providing indicia that the assembled component has been acceptably manufactured, even though adhesive is present in the desired location. For example, a hot melt adhesive applied to a box or other inner flap will clearly register on an infrared (IR) or related thermal image, even in situations where the outer flap may not have been properly adhered to the inner flap of the assembly before the adhesive cooled and set. As such, the mere detection by such a system would incorrectly give the appearance of a successfully glued component, even in situations where such is not the case. This difficulty is compounded by the fact that assembling equipment and related forming machines have tight space constraints, making it difficult to monitor actual adhesive placement immediately after it is applied.

SUMMARY OF THE INVENTION

A system for checking the quality of applied hot melt adhesive to a substrate according to an aspect of the present invention may include acquiring at least a thermal (i.e., IR-based) image. In one form, such an image may in and of itself include information to make an accurate determination of the geometric features of the object that has received the deposited hot melt. In other words, a geometric image or registration of the object may be made from clues in the acquired thermal image. In another form, this geometric information may be acquired from other sensed information, such as that in the form of one or more images received from the visible spectrum (such as through a camera or related device), laser time of flight (LiDAR), structured light camera or Time-of-Flight camera. In particular, LiDAR methods build a 3D map of a field of view by sending short-pulsed, narrow laser beams and measuring the time of the return reflection. By continuously scanning a field of view in a grid pattern, the TOF measurement system can build up a series of distances to different points in the field and reconstruct the field topography. More precise measurements can be made at closer range by incorporating triangulation of signals from multiple sources. Structured light systems project a laser beam or similar well-defined light pattern, and then image the projected wide laser beam with a visible light camera (either line scan or area scan). The curves and changes in the normally straight laser line projection describe the topography of the surface onto which the laser light is projected. By scanning an entire surface and taking sequential images of each new light position, a complete 3D map of a surface can be generated. Time of Flight cameras use single point (usually LED), pulsed illumination and measure the time from the light pulse to its reflected return to the sensor array. Distance is calculated based on the time measurements, and is calculated to each pixel of the sensor array to be used to build a topographical map of the subject.

According to a first aspect of the invention, a system for checking the quality of applied hot melt adhesive to a substrate is disclosed. The system includes one or more imaging devices (also referred to herein as an imager, imaging detector or the like) that can receive a visually-identifiable image of the passing assembled object, as well as an IR camera that can receive a thermal image of the assembled object. Such IR imaging is capable of detecting hot melt signatures irrespective of whether the surface upon which the adhesive is deposited is exposed or covered, assuming that in the latter, the flap, fold or related covering that renders the deposited hot melt visually opaque is in fact thermally conductive to permit the heat emanating from the deposited adhesive to reach the IR portion of the imaging device. This in turn allows the imaging device to be able to "see" through some opaque surfaces of an assembled object as long as they conduct heat sufficiently to allow the adhesive to be visible in contrast to the environmental and workpiece temperatures. Moreover, by the use of sensors or related detection devices within various bands of the electromagnetic spectrum in general and the visible (400 to 700 nanometer) band and thermal (for example, roughly 700 nanometer to 13,000 nanometer) band in particular, coupled with software or a related algorithm, images may be retrieved, stored, mapped, overlayed and processed as a way to verify that the adhesive deposition is taking place in accordance with predetermined objectives, for example, for an as-folded container. In one exemplary form where the adhesive is deposited as one or more beads, the system can be used to determine the correct number and position of each. Additional components, including one or more filters and one or more imaging devices, may be included.

According to another aspect of the invention, a method for inspecting hot melt adhesive applied to a substrate is disclosed. The method includes placing the substrate with the hot melt within the detection range of one or more imaging devices such that signals received from the imaging device (or devices) contain thermal images of the hot melt, as well as a geometric representation of the substrate. The imaging device (or a controller cooperative with the imaging device) processes signals such that a composite representation of the substrate with the hot melt is created. From this, software, computer-based code or a related algorithm may be used to determine if the composite representation satisfies predetermined criteria for deposition criteria for the substrate. After this, notification may be provided that the substrate with the hot melt should be accepted or rejected based on the determination of whether the hot melt has been deposited in compliance with the predetermined criteria. Images in the aforementioned visually-identifiable image correspond to signals received by the imaging device that are within the visible spectrum; such signals contain information needed to form a geometric representation of the substrate, where the terms "geometric representation", "geometric feature", "geometric image" or the like comprises any pictoral, data, mathematical or other representation that allows the detected features to be modeled, viewed or reproduced in 2D or 3D space to allow subsequent user or machine visualization or related use. The approach of at least this embodiment of the present invention allows not only inspection of deposited hot melt on as-yet unassembled substrates where readily-visible indicia of adhesive deposition is available, but also on substrates that have already been assembled such that various deposition locations of the hot melt may be obscured from view.

According to yet another aspect of the invention, a method for assembling a product from a blank is disclosed. The method includes receiving the blank into a processing machine such that hot melt is deposited on one or more of the blank's surfaces. After this, the assembly of the product is completed so that the adhesive deposited thereon is placed in contact with another of the blank's surfaces or an additional component such that they become adhesively bonded. In another form, the blank may have adhesive placed thereon such that it constitutes the completion of the assembly process such as that associated with hot melt potting applications. Next, the adhesively-contacted surfaces are placed within detection range of one or more imagers that receive both an IR image and a geometric representation of the assembled product from the box such that at least the adhesively-contacted surfaces are introduced into an imaging device or related signal-processing equipment. From this, the device (which may be computer-controlled, for example) makes a determination of whether a representation of the images that correspond to the adhesively-contacted surfaces satisfies a predetermined criteria for acceptable adhesive quality. In the event that the adhesively-contacted surfaces satisfy the predetermined criteria, the device will provide notification that the assembled product should be accepted for its intended use. Likewise, in the event that the adhesively-contacted surfaces do not satisfy the predetermined criteria, the device will provide notification that the assembled product should be rejected such that it can be subsequently withdrawn from further assembly or use.

It will be appreciated by those skilled in the art that in all of the aforementioned aspects, surface temperature contrast is required to enable an IR image to "see" anything. As such, the outline of the substrate (for example, a box substrate) that shows edges or corners at a different temperature than the air or other ambient environment around the outline defined by the substrate will constitute the necessary bright spot or shadow that can be used by the imager. Accuracy is further enhanced when the substrate being inspected is always presented to the imager in the same orientation and position; such repeatability can be ensured by an indexing conveyor or like equipment so that deposited adhesive lines or dots can be expected to be in the same spot every time regardless of where the edge of the substrate is.

BRIEF DESCRIPTION OF THE DRAWINGS

The following detailed description of the present invention can be best understood when read in conjunction with the following drawings, where like structure is indicated with like reference numerals and in which.

DETAILED DESCRIPTION OF THE PREFERRED EMBODIMENTS

Figure 1:
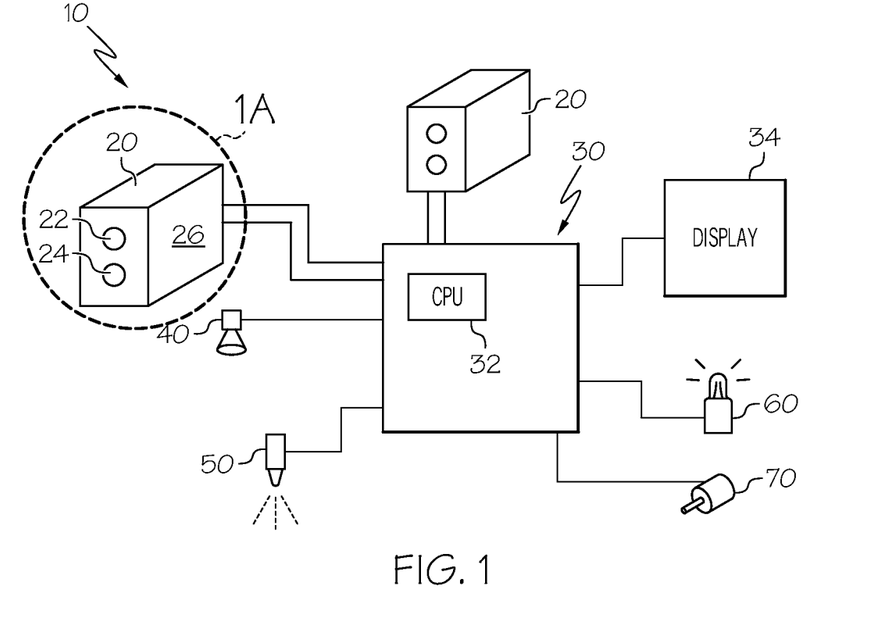
FIG. 1 is a block diagram showing an arrangement of components used in a hot melt inspection system according to an aspect of the present invention.
Figure 1A:
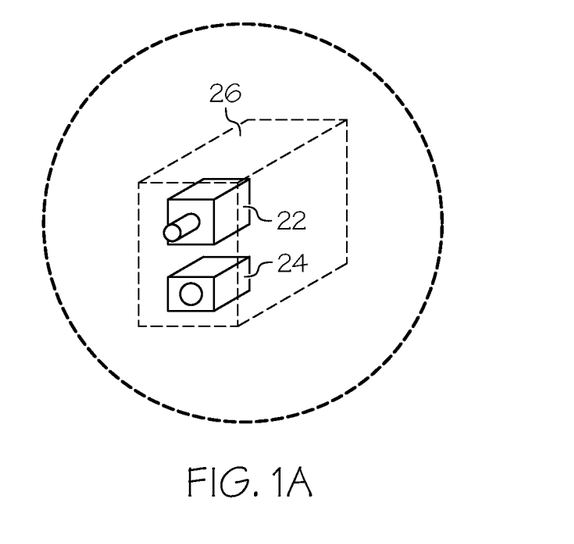
FIG. 1A is a detail view taken from FIG. 1 highlighting a heat-sensitive camera and an optically-sensitive camera within a common enclosure.
Figure 2A:
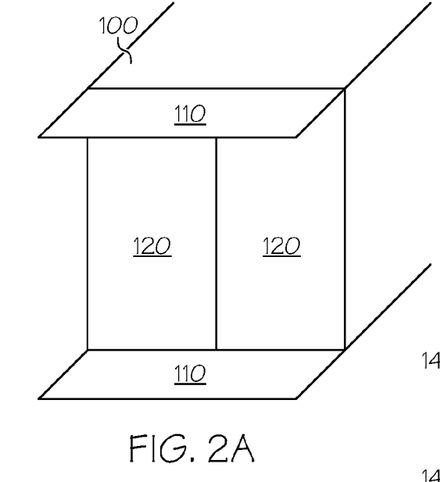
FIG. 2A shows a portion of a case or carton sealing process where the inspection system of FIG. 1 is being used on a carton as it is filled and closed or assembled, highlighting flap locations on the carton prior to the application of adhesive.
Figure 2B:
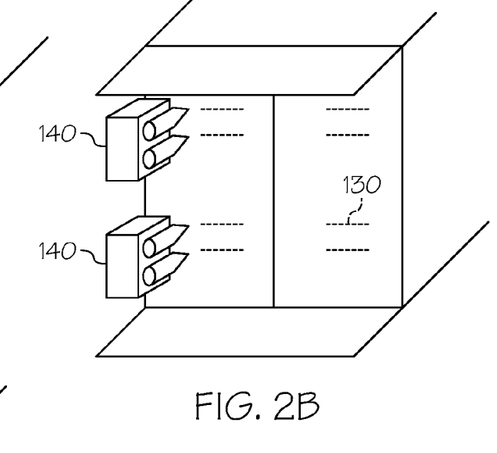
FIG. 2B shows the case or carton of FIG. 2A once adhesive has been applied.
Figure 2C:
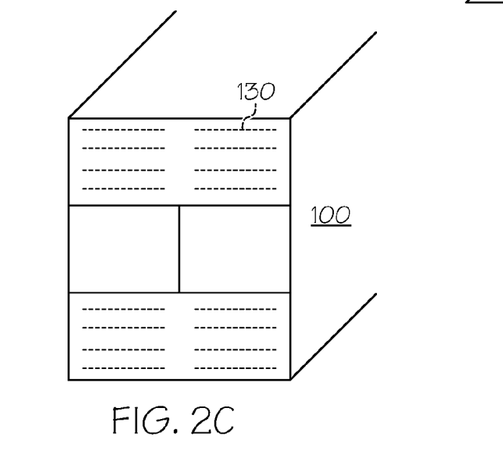
FIG. 2C shows the case or carton of FIG. 2B once flaps have been folded over onto the exposed adhesive.
Figure 2D:
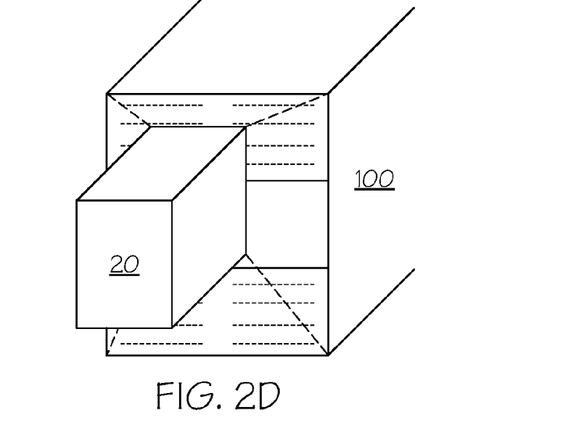
FIG. 2D shows the case or carton of FIG. 2C being inspected with the hot melt inspection system of FIG. 1.

Referring initially to FIGS. 1 and 1A, a block diagram highlights the major components of the inspection system 10 according to an aspect of the present invention. One or more imaging devices 20 (which will be discussed in more detail below) are used to detect the presence of hot melt, as well as an object to which the hot melt is applied. A controller 30 coordinates the hot melt inspection operations of the one or more imaging devices 20 by not only receiving images that have been detected by the imaging devices 20, but also by algorithmically manipulating the data that corresponds to the received images in order to provide machine-usable or human-usable information output. Significantly, the approach of the various aspects of the present invention enable common errors associated with folding, gluing or related object assembly to be identified at the end of the object manufacturing process in a way not possible with approaches that are only configured to identify exposed adhesive in an interim forming step. In one form, controller 30 may be equipped with input, output (neither of which are shown) and a central processing unit (CPU) 32 (also known as a processor), and content-addressable memory (for example, in the form of read-only memory (ROM) for storing a program which controls the operation of the overall apparatus, and a random-access memory (RAM) having a data storage area (neither of which are shown). The CPU 32 is connected to the input and output through an appropriate interface (which may perform one or both of discrete and analog input and output), while additional signal-processing apparatus, such as an analog-to-digital (A/D) converter (not shown). The CPU 32 also communicates with the imaging devices over a network. These components cooperate to permit controller 30 to have access to digital storage allowing visual images of either failed or good products to be reviewed. Such a controller 30 may function as a digital signal processor, an application specific integrated circuit (ASIC), a field programmable gate array, any suitable programmable logic device (such as a programmable logic controller (PLC)), discrete gate or transistor logic, discrete hardware components, or any combination thereof. In one preferred form, the controller 30 is configured to operate upon an algorithm which may be loaded into ROM (for a specific-purpose controller) or RAM (for a general-purpose computational device) to determine the presence of the deposited hot melt. In one particular form, the algorithm may be embodied as computer-executable instructions (such as program modules, whether as routines, programs, objects, components, data structures or other elements that perform particular tasks or implement particular data types) for ROM or RAM, or in any other suitable memory structure such as flash memory, EPROM memory, EEPROM memory, registers, hard disks, removable disks, CD-ROM or the like. In the alternative, the storage medium may be integral to the processor (for example, as part of the aforementioned ASIC) such as that used on a chip designed to run a cellular telephone. Controller 30 preferably embodies significant attributes of a computer system based on a von Neumann architecture such that it may mimic a general purpose or stored-program computer. Likewise, controller 30 may be configured as a particularly-adapted computer or computer-related data processing device that employs the salient features of a von Neumann architecture in order to perform at least some of the data acquisition, manipulation or related computational functions discussed herein.

A display unit 34 cooperates with controller 30 to provide indicia to a user about the status of the hot melt, as well as its placement on or in the object to which the hot melt is applied. In particular, it conveys a two dimensional (2-D) image or scan of each assembled object that passes by imaging device 20. It will be appreciated by those skilled in the art that display unit 34 may also serve as the interface discussed above in situations where it includes touch screen functionality. Display unit 34 may additionally display images from the multiple bands (for example, optical and IR) in order to provide an overlaid image that allows a user to readily identify deviations in the formed object. Display unit 34 is also capable of receiving digital or analog electrical signals representative of desired system settings related to (among other things) adhesive or target parameters, tolerances, machine status and other performance-related criteria.

Additional equipment improves the functionality of system 10, to allow it to not just measure and detect the images emanating from the assembled object, but also to provide notice (to either a user or a fabrication machine to which system 10 is cooperative) as to variances from desired target parameters of the object, as well as to send a rejection signal to the fabrication machine of a defective finished object, in addition to optionally storing a representation of such data for archival purposes and or subsequent analysis. Such equipment includes a photo-eye trigger 40 that may be used to detect the presence of the object on a conveyor or related assembly platform, a marking valve 50 or related mechanism that can be used to affix readable indicia upon the object being assembled, one or more alarms 60 to provide notification of an out-of-specification condition, and an encoder or speed-measuring device 70 to adjust the delivery speed of a conveyor or other delivery platform to promote proper alignment and other parameters necessary for accurate object feeding, as well as accelerating or retarding equipment to adjust the speed at which the object moves through it assembly steps. Additional features may also be included, such as a reject mechanism to remove or divert a defectively-assembled object from the fabrication machinery.

The cooperation of imaging device or devices 20 and controller 30 (which together—possibly in conjunction with other ancillary equipment such as that discussed above—make up inspection system 10) can be used to assess the quality of the assembled object. Significantly, unlike systems that only measure exposed adhesive, the present invention allows detection to take place after the object has been closed or otherwise assembled, so long as the heat from the adhesive conducts through the folded-over portions of the assembled object to reveal the position of the applied bead of adhesive underneath. Likewise, the use of a sensor (for example, a camera) in the optical waveband or a laser profiler allows the position of the hot melt to be shown on a display relative to distinguishing features of the object (such as edges, folds or the like) to facilitate use by a human operator. As such, imaging device 20 may be configured with a first imaging device in the form of a heat-sensitive camera 22 and a second imaging device in the form of an optically-sensitive camera 24 within a common enclosure 26. In another embodiment, imaging device 20 may be configured with a first imaging device in the form of a heat-sensitive camera 22 and a second imaging device in the form of a laser profiler, a structured light camera or other structure. In situations where a laser profiler system is used, a laser beam is projected onto a surface and together with a digital camera is able to detect the shape and size of features on an object. As such, this technology substitutes for visible images by accurately measuring specific geometric portions of an object. Likewise, structured light cameras use various light sources and a series of images to create shadows that yield computations with 3D information. By analyzing the 3D information, geometric features can be recognized. Laser time-of-flight cameras also are suitable for measuring surface features on a product to be glued and have the advantage of taking measurements very quickly. Pixels on the camera measure the time it takes light to travel to the target object and back. Algorithms assemble this phase-shifted data into viewable images. Thus, the 3D information is acquired by the imaging device 20 configured as a 3D profile imager (i.e., profiler) that locates object features by their depth; such a configuration acts as a 3D imaging camera as a way to detect carton or case edges for glue registration. Moreover, such a system uses the 3D imaging for detection of proper flap compression, damaged or crushed flaps or missing handles, diecuts or other physical features on the case or carton. Such a hot melt detection approach—with its enhanced ability to determine object geometry—benefits from the combination of IR image gathering and 3D or visible data collection to detect hot melt beads which, in packaging, can otherwise be hard very hard to ascertain.

As mentioned above, imaging device 20 receives signals from respective cameras or related sensors 22 and 24 that are configured to pick up signals in different portions of the electromagnetic spectrum in order to determine if the representation of the deposited adhesive satisfies a predetermined criteria established for the assembled object. In one optional form, filters may be placed in cooperation with the IR camera 22 such that passage of a signal that corresponds to selective bands within a high temperature range may be allowed. By using two or more different filters, a single IR camera 22 can be used for more precise hot melt glue detection without the need for redundant equipment. Regardless of whether filtering is used to acquire discrete regions within the IR band, the combination of the visual or 3D and IR images retrieved by the imaging device 20 and that are operated upon by the controller 30 may be used to determine if predetermined deposition criteria relating to adhesive deposition patterns, quantities or the like are either inside or outside of permissible norms. In one preferred form, the predetermined deposition criteria may be stored in memory (as discussed above) such that the norms preserved therein may be used as a comparison against the sensed information.

In one form, the imaging device 20 may use active illumination equipment, such as a source (not shown) of electromagnetic radiation in the one or more of the non-IR wavelengths of interest discussed above. Such illumination equipment may include all of the electro-optical components and associated conditioning components to send and receive data signals, control signals or the like. As with other features that are subject to interaction with—or control by—controller 30, the illumination equipment may be computer-controlled to take into consideration the parameters associated with capturing the one or more images. Such illumination equipment may be particularly useful in the optical band, where otherwise there may be an inadequate level of background lighting needed to capture a suitable image. In such case, the illumination equipment may include a printed circuit board (PCB) to provide power, timing and related conditioning circuitry for the light emitters and other ancillary components. In a preferred embodiment, illumination wavelengths can be chosen to correspond to those signals deemed important for receipt into imaging device 20 as well as those suitable for conversion to user-recognizable format within the optical waveband that may be depicted on display unit 34. It will be appreciated by those skilled in the art that, given the deposited glue is possessive of its own heat, the use of active illumination equipment as discussed above for the aforementioned IR band is neither needed nor desired.

As mentioned above, hot melt and related adhesive deposition takes place either discretely or continuously. Moreover, there are numerous classes of machines where the inspection system 10 of FIG. 1 may be used to perform these discrete and continuous functions. Referring next to FIGS. 2A through 2D, one such class involves packaging machines such as case sealers, carton sealers or the like that take advantage of discrete hot melt adhesive application techniques where boxes 100 and related packaging with foldable flaps 110 are held together with such adhesive 120. Such machinery may be configured to deposit the adhesive 120 in a vertical stream, while others may be configured to deposit it in a horizontal stream or any angle therebetween; in all configurations, the purpose is to glue and close the flaps 110 that hold the box 100 together. In particular, a carton packaging application is shown with a notional adhesive deposition and inspection taking place on a vertical surface of the carton. It will be appreciated by those skilled in the art that in many cases, boxes 100 have already been "produced" by a folder gluer (not shown) or related machine such that the body panels have been glued together at a manufacturer's joint forming essentially a "tube" or Regular-Slotted-Carton (RSC), while other boxes 100 are constructed in the machine by wrapping or forming the box 100 around the product, in which case a non-glued blank is used. In either case, it would be advantageous to be able to visualize the adhesive 120 deposition pattern beneath the closed flaps 110 to confirm that adhesion has taken place as long as the adhesive 120 was applied to the opposite flap 110 and has transferred its heat to the outside to be viewed by system 10. Significantly, if adhesive 120 is applied to the outside flap 110, inspection isn't necessarily able to verify by the heat signature if the flap 110 is securely closed. Referring first to step (a) in FIG. 2A, a carton or case in the form of a box 100 with major flaps 110 open and minor flaps 120 closed; in this example, the box 100 is already filled with product, such as cans, bottles or other containers. Referring next to step (b) in FIG. 2B, hot melt 130 is applied onto one or more surfaces that correspond to the minor flaps 120; the hot melt 130 is dispensed through a conventional dispensing mechanism, such as a valve 140. Referring next to step (c) in FIG. 2C, the major flaps 110 of the filled box 100 are folded over into a closed position; although obscured from view, the heat from the hot melt 130 that is used to bind the flaps together is sufficient to radiate through the closed major flaps 110. Referring next to step (d) in FIG. 2D, the assembled box 100 is passed within detection range of imaging device 20 in order to receive the radiated heat, as well as to receive an image of at least one of the box 100 or flaps 110, 120 so that a geometric representation is obtained that may be used to overlay with the radiated hot melt. Although discussed in conjunction with the minor flaps 120, embodiments of the present invention may be used to apply adhesive to the major flaps 110, either in addition to or in place of, the minor flaps 120, as both forms are deemed to be within the scope of the present invention.

In other embodiments of packaging machines (not shown), the open flaps 110, 120 may be on one or both sides of the box, carton or case 100 and the product to be packaged slid inside. In this circumstance, the minor and major flaps 110, 120 are glued with horizontal beads of adhesive 130. In other configurations (also not shown), trays are produced with a plunger mechanism converting a scored sheet of carton or corrugated stock and gluing the corners just prior to the plunge. In wrap-around machine configurations, the product to be packaged stops on the conveyor and the carton blank is formed around the product and the joints are glued in a variety of orientations. Certain box styles (for example, Bliss boxes (not shown)) are assembled in the machine from panels that are folded and glued as the box is assembled. As with the embodiment depicted in FIGS. 2A through 2D, the difficulty of inspecting the finished glue joints of such configurations using traditional techniques (which are covered up very quickly) in all of these cases is averted, as the present invention permits adhesive inspection after assembly of the box or related carton or case 100. Examples such as this are not meant to be exhaustive; accordingly, the use of different types of packaging (including those with dividers, self-erecting dividers, octagonal or other non-traditional shapes) is also deemed to be within the scope of the present invention. As such, the steps discussed herein relative to the fabrication of a box, carton, corrugated or other such container or package is intended for illustration only, and that the creation of any article formed through one or more of the operations discussed herein is likewise deemed to be within the scope of the present invention.

Figure 3:
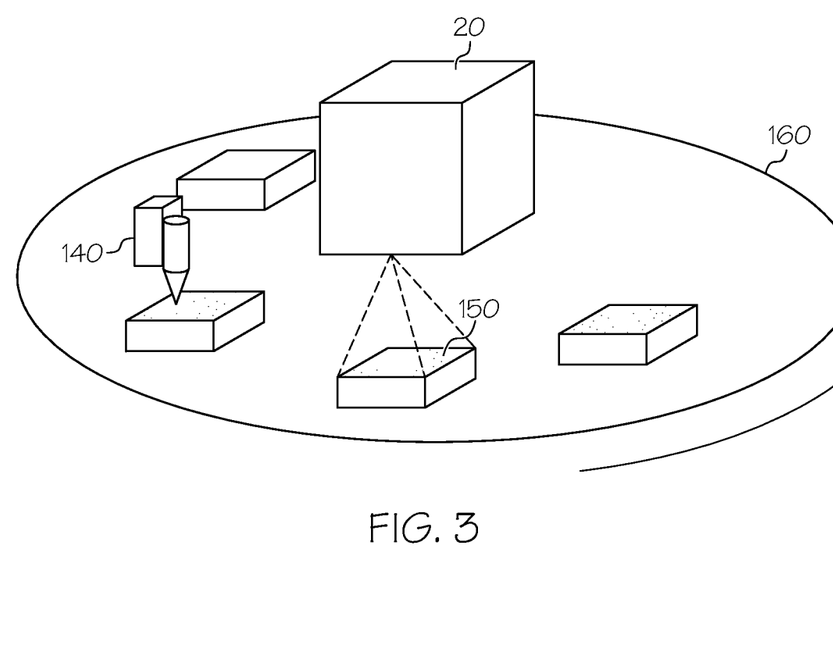
FIG. 3 shows assembly inspection used in conjunction with a rotary indexing table where discrete product assembly in a non-conveyor environment is used.

Referring next to FIG. 3, another class of machines that may take advantage of the inspection system 10 of FIG. 1 involves product assembly. As with the machines discussed in conjunction with FIG. 2 above, these machines also use discrete adhesive deposition, but may (in certain circumstances) also use continuous deposition. In this instance, substrates that are configured to receive hot melt could be in suitable forms, even if not planar. Such substrates may include those configured to receive and contain a specified volume of hot melt Likewise, examples of machines include those used to deposit hot melt as a potting agent in a carrousel-based configuration (as shown) or a sliding two-position situation (not shown). Other examples include machines used to assemble furniture, machines used to coat the inside of multi-strand cables to reduce the likelihood of insulation pull, as well as machines use in the assembly of plastic boxes or the like. Whether in the form of potting, dots or puddles of hot melt to attach another component, the hot melt is quick-setting and useful for repetitive assembly in the pharmaceutical industry, the medical industry including test strips, potting of electronic products and cable connectors, cosmetics assembly, cap-wadding and sealing, or the like. The extent to which the heat signature of the adhesive provides an indication that glue has been deposited, the system of FIG. 3 can identify the presence and location of the adhesive relative to geometric features on the part or substrate being glued.

Figure 4:
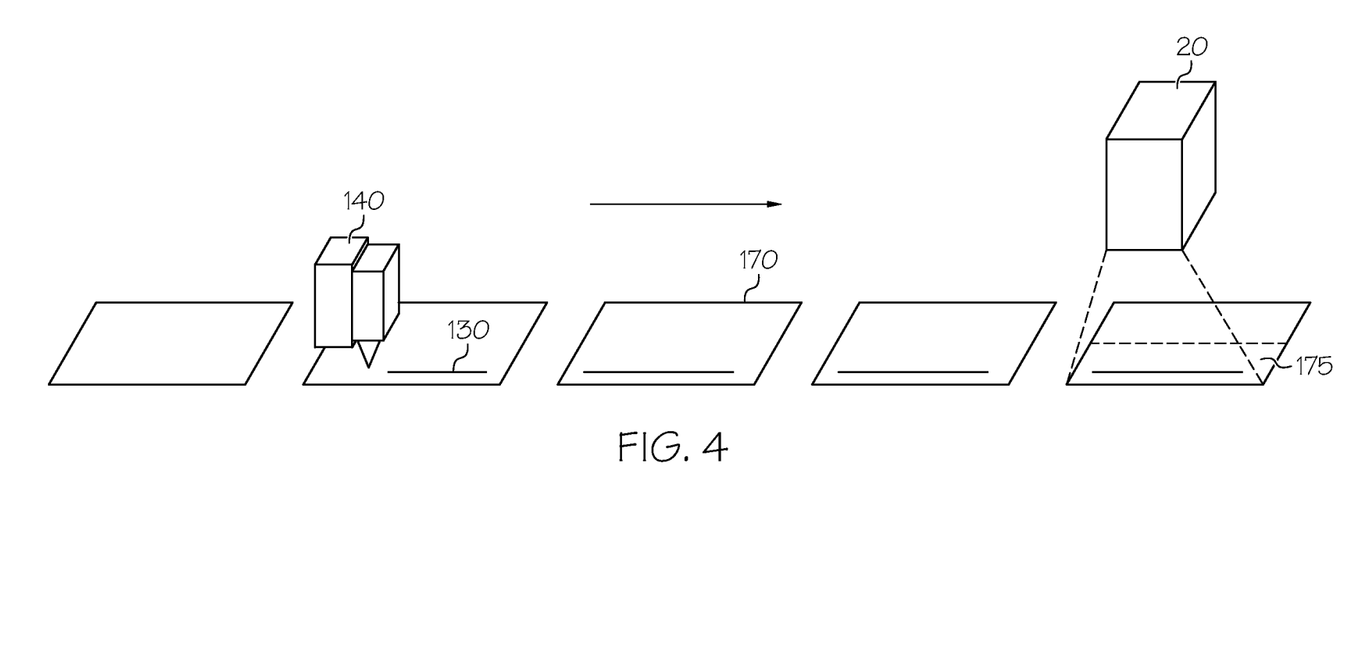
FIG. 4 shows inspection of hot melt applied discretely to a substrate moving along a general purpose conveyor.

Referring next to FIG. 4, still another class of machines usable with the inspection system 10 of FIG. 1 is known as converting machinery, where discrete hot melt is placed onto a paper, plastic or wood product 170 in order to convert it into another product. In this case, the hot melt may or may not be covered. In some cases a liner would be applied over the top of the hot melted adhesive 130 to protect it for later use (such as in a peel-and-seal envelope or the like) where a removable strip (not shown) with a generally non-adhesive surface can be removed to expose a gummed or other adhesive surface. In other cases, the product 170 may be folded as part of its construction, where in one form a flap 175 can be placed over the melted adhesive 130. In situations such as these, it would be beneficial to have the inspection system 10 be able to "see" through the covering material. In other cases, the hot melt adhesive 130 may be exposed Likewise, the production of books that involves depositing hot melt in certain discrete areas to the pages of binding of a book could be verified using this technique.

In one particular form, the system of FIG. 4 may cooperate with the blanks used to make the assembled object; such blanks may be of corrugated paper or related sheet ranging from a single layer of approximately 0.05 millimeters (mm) thick up to a larger, single-wall corrugated (where the flute size is up to approximately 5 mm). In other forms (depending on the need), the substrate may be made from other materials as well, including, plastic, wood, composites or the like, so long as the material retains its ability to transmit thermal images through one or more layers. The hot melt valves 140 act as gluing stations to deposit adhesive 130 along at least a portion of the length of one of the surfaces adjacent the edges, and can do so as an array of individual dots or as a continuous line. As will be appreciated by those skilled in the art, the hot melt valves 140 can be configured to deposit top down, sideways or any other suitable orientation and can deposit beads, spray patterns, ribbon-coat patterns and dot patterns. As discussed previously, the thermal signature of the hot melt adhesive 130 can be seen by the IR-sensitive part of imaging device 20 in the inspection part of the assembly operation. The sensed image may then be sent to the controller 30 for subsequent signal processing, analysis and reporting. As before, the product 170 can be imaged either immediately after hot melt deposition and before being covered, or after being assembled by looking at the heat signature of the object that covers the hot melt.

Figure 5:
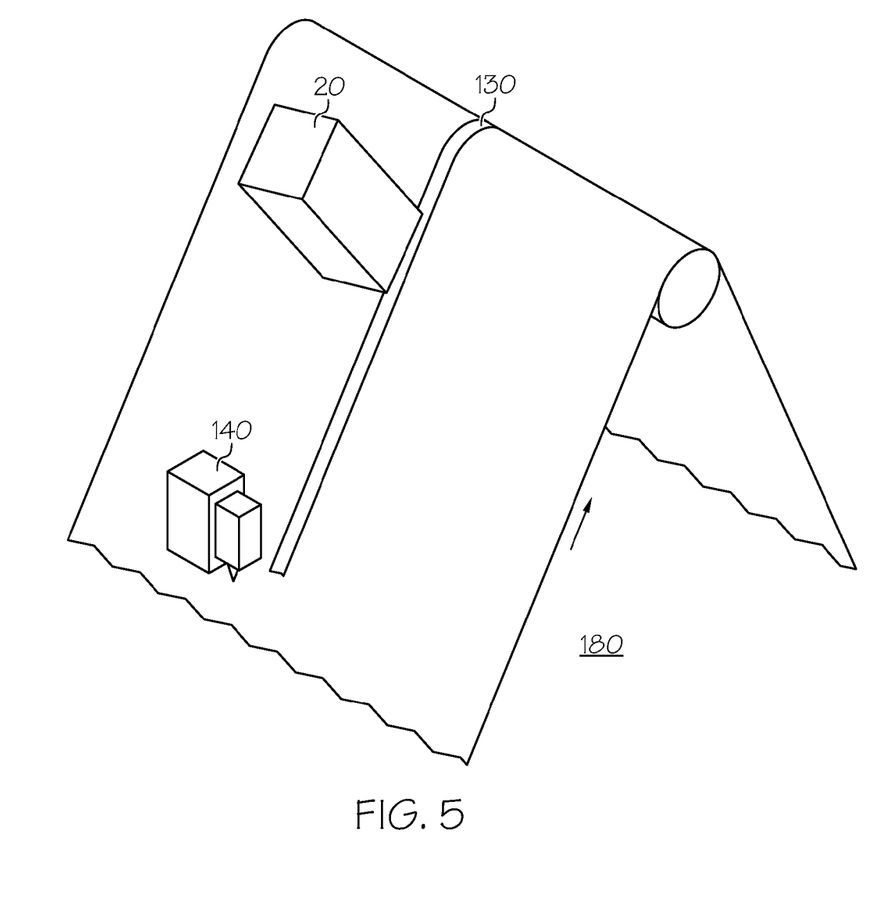
FIG. 5 shows inspection of hot melt applied continuously to web handling equipment where the glue is applied in a continuous rather than discrete pattern.

Referring with particularity to FIG. 5, details associated with continuous substrate adhesion or related assembly is shown. In one particular form, webs of plastic or paper may be loaded into a suitable unwinder, printed or otherwise converted with coatings or the like and have hot melt adhesive applied to one or both sides for the purposes of later applying the plastic or paper to another object after being die-cut or for the purposes of being used as a release paper for other label products or laminates. The hot melt valve or valves 140 apply adhesive along web 180 as it travels past, producing bead, spray or coating 130. As discussed previously, the thermal signature of the hot melt adhesive 130 can be seen by the IR-sensitive part of imaging device 20 in the inspection part of the assembly operation. As before, the sensed image may then be sent to the controller 30 for subsequent signal processing, analysis and reporting. In this way, the application exemplified by the system of FIG. 5 emulates the converting machinery of FIG. 4, except now in a continuous (rather than discrete) form. Such hot melt deposition may often by spraying or coating. Such machinery may include that used for paper substrates, such as used for printed commercial material with hot melt tack for certain pages or foldouts, mailers with hot melt-tacked fold-outs, self-adhesive label manufacture, etc. or the like. As with the previously-discussed class of machines, the deposited hot melt may be covered or not.

Figure 6:
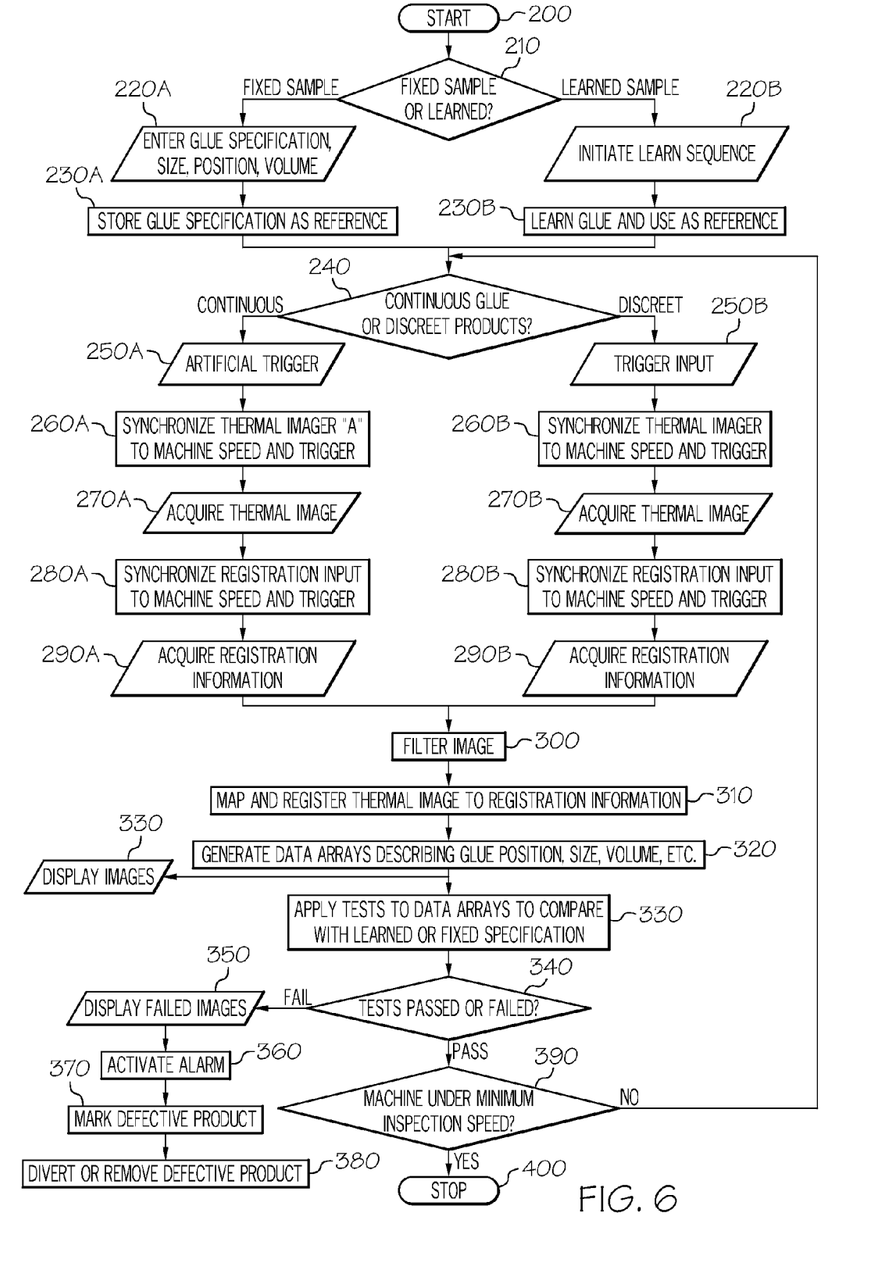
FIG. 6 is a flowchart for determining the acceptability of an adhesively-assembled object that has been subjected to a forming process.

Referring next to FIG. 6, the steps used to determine the acceptability of an object to which hot melt is applied as part of an assembly of the object is disclosed. In one form, the steps depicted herein may be embodied in the form of an algorithm loaded into or otherwise cooperative with controller 30 through memory (such as the aforementioned ROM or RAM). At the start 200 of operation of system 10, a determination is made of whether the standard is fixed or learned 210. In the present context, a fixed sample is submitted to the system as a standard ahead of time and denotes specific locations of glue and sizes of beads where appropriate. By contrast, a learned sample uses an image selected by the user or automatically to be used as the "standard" in evaluating all future images. Fixed samples may be usable with this method as the moments of inertia or other locating descriptors could be used to tell the system where glue should be. In situations where the sample is fixed, glue specification, size, position and volume is input either from specification sheets or stored as "jobs" in the controller, 220A; this information is then stored as a reference 230A. In situations where the sample is learned, a learn sequence is initiated 220B, and this in turn is used as a reference 230B. Once the appropriate determination of the fixed or learned nature of the sample is complete, a determination is made as to whether continuous glue or discrete application 240 is to be employed. In cases where the application is continuous, an artificial trigger 250A is used to divide the continuous images into blocks than can be separately evaluated. In some cases, alternating imagers would be required to allow time for the algorithm to evaluate the first image while collecting the second. The trigger is not coming from the machine but is generated by the control to time the start and stop of image data collection and synchronize downstream activities such as marking, diverting, or the like. After that, a first thermal imager "A" is synchronized to the speed of the machine and trigger 260A, and then a thermal image is acquired 270A. Thus, an encoder monitors how much product has passed since the trigger and how far apart the trigger is from the imager. The speed is necessary as when the image acquisition is finished, the imager has to be prepared for the next image capture in the proper position. In present IR imager configurations, the IR imager—because of its inherent "warmup" time for the arrays—requires continuous capture; as such, the window that is being captured must be marked and the speed of the passing product kept track of for correct image acquisition. Such an approach is useful in order to avoid errors by simply beginning imaging and continuing to do so until turned off. It will be appreciated by those skilled in the art that IR imager configurations where such warmup and continuous capture are not required are likewise compatible, and as such are deemed to be within the scope of the presently disclosed invention. From this, registration input is synchronized to machine speed and trigger 280A, and then the registration information is acquired 290A. Likewise, in cases where the application is discrete, trigger input 250B is received, after which the thermal imager is synchronized to the machine speed and trigger 260B. Again, a thermal image is acquired 270B and then registration input is synchronized to machine speed and trigger 280B, after which registration information is acquired 290B. Once these steps are complete, the image may be filtered 300, mapped and registered to the registration information 310, and then data arrays describing glue position, size, volume and related information are generated 320. This may be sent to display 34 in a separate step 330. In addition, a determination must be made to see how the data arrays compare to the deposition criteria of a learned or fixed specification 340. In situations where the test fails (i.e., the hot melt deposition is not in conformance with predetermined standards) an indication of a failed image 350 is made, and then an alarm is activated 360, after which the defective product is marked or otherwise identified 370, and then diverted or removed 380 from the assembly process. On the other hand, if the inspected product passes, it must subsequently be determined if the fabrication machine or other processing platform is operating under minimum inspection speed 390; if yes, then the inspection is at an end 400; if not, it is sent back to step 240.

It is noted that recitations herein of a component of an embodiment being "configured" in a particular way or to embody a particular property, or function in a particular manner, are structural recitations as opposed to recitations of intended use. More specifically, the references herein to the manner in which a component is "configured" denotes an existing physical condition of the component and, as such, is to be taken as a definite recitation of the structural factors of the component. Likewise, it is noted that terms like "generally," "commonly," and "typically," when utilized herein, are not utilized to limit the scope of the claimed embodiments or to imply that certain features are critical, essential, or even important to the structure or function of the claimed embodiments. Rather, these terms are merely intended to identify particular aspects of an embodiment or to emphasize alternative or additional features that may or may not be utilized in a particular embodiment.

For the purposes of describing and defining embodiments herein it is noted that the terms "substantially," "significantly," and "approximately" are utilized herein to represent the inherent degree of uncertainty that may be attributed to any quantitative comparison, value, measurement, or other representation. The terms "substantially," "significantly," and "approximately" are also utilized herein to represent the degree by which a quantitative representation may vary from a stated reference without resulting in a change in the basic function of the subject matter at issue.

Having described embodiments of the present invention in detail, and by reference to specific embodiments thereof, it will be apparent that modifications and variations are possible without departing from the scope of the embodiments defined in the appended claims. More specifically, although some aspects of embodiments of the present invention are identified herein as preferred or particularly advantageous, it is contemplated that the embodiments of the present invention are not necessarily limited to these preferred aspects.

What is claimed is:

1. A system for checking the quality of hot melt applied onto an object that is assembled with said hot melt, said system comprising:
    an imaging device responsive to both a thermal image that emanates from said hot melt and a multi-dimensional image which is representative of a geometric feature associated with said object;
    a controller comprising a processing device cooperative with said imaging device to determine if signals received therefrom that correspond to said applied hot melt and said at least one geometric feature meet predetermined deposition criteria for said assembled object; and
    a timing mechanism cooperative with said controller to determine a length of time between deposition of said hot melt on said object and arrival of said object to within sensing range of said imaging device;
    a notification device responsive to said processing device to provide indicia of whether said predetermined deposition criteria is met.

2. The system of claim 1, wherein said imaging device comprises a first imaging device that is responsive to said thermal image and a second imaging device that is responsive to said multi-dimensional image.

3. The system of claim 2, wherein said second imaging device is selected from the group consisting of at least one camera configured to receive images within the visual band of the electromagnetic spectrum, 2D imaging devices, 3D imaging devices and a separate thermal image camera.

4. The system of claim 3, wherein said 3D imaging device comprises a 3D profile imager that locates object features by their depth.

5. The system of claim 2, wherein said first imaging device operates via thermal contrast between said hot melt and at least one surface of said assembled object.

6. The system of claim 2, further comprising a photo-electric sensor cooperative with said first and second imaging devices to provide a triggering mechanism for detection of said received signals.

7. The system of claim 2, wherein the first imaging device is sensitive to energy in the infrared band with a wavelength range of between about 5000 nm and about 13,000 nm.

8. The system of claim 2, wherein said notification device comprises a display mechanism that depicts an overlay representation of images from both of said first and second imaging devices for the purpose of locating said hot melt with respect to said at least one feature on said assembled object.

9. The system of claim 1, further comprising a rejection mechanism cooperative with said controller such that upon determination by said system that said predetermined deposition criteria is not met, said rejection mechanism removes said assembled object from further assembly.

10. The system of claim 1, wherein said predetermined deposition criteria comprises at least one of quantity and location of said hot melt on said assembled object.

11. A system for checking the quality of hot melt applied onto an object that is assembled with said hot melt, said system comprising:
  an imaging device with a thermal image detection component and a geometric feature detection component, wherein the thermal image detection component is signally cooperative with heat data that emanates from said hot melt and the geometric feature detection component is signally cooperative with said pictorial data that corresponds to said object;
  a controller cooperative with said imaging device to determine if images from both of said components that correspond to said applied hot melt and said at least one geometric feature meet predetermined deposition criteria for said assembled object;
  a timing mechanism cooperative with said controller to determine a length of time between deposition of said hot melt on said object and arrival of said object to within sensing range of said imaging device; and
  a notification device responsive to said controller to provide indicia of whether said predetermined deposition criteria is met.

12. The system of claim 11, wherein at least one of said timing mechanism and said controller provides indicia of when a predetermined time delay associated with deposition of said hot melt has been exceeded.

13. The system of claim 11, wherein said geometric feature detection component comprises at least one camera configured to receive images within the visual band of the electromagnetic spectrum.

14. A system for checking the quality of hot melt applied onto an object that is assembled with said hot melt, said system comprising:
  an imaging device comprising:
    a first imaging component responsive to a thermal image that emanates from said hot melt; and
    a second imaging component operating in the visible band and responsive to an image that is representative of a geometric feature associated with said object;
  a controller cooperative with said imaging device to determine if a combination of signals received therefrom and that are represented by said thermal image of said hot melt and said geometric feature of said object meet predetermined deposition criteria;
  a timing mechanism cooperative with said controller to determine a length of time between deposition of said hot melt on said object and arrival of said object to within sensing range of said imaging device;
  a photo-electric sensor cooperative with said imaging device and said controller to provide a triggering mechanism for detection of said images; and
  a notification device responsive to said controller to provide indicia of whether said predetermined deposition criteria is met.

15. The system of claim 14, wherein said second imaging component comprises at least one camera configured to receive images within the visible band of the electromagnetic spectrum.

* * * * *